US009095646B2

(12) United States Patent
Chow et al.

(10) Patent No.: US 9,095,646 B2
(45) Date of Patent: Aug. 4, 2015

(54) DEVICES AND METHODS FOR TRANSNASAL DILATION AND IRRIGATION OF THE SINUSES

(75) Inventors: Mina W. B. Chow, Campbell, CA (US); Hung V. Ha, San Jose, CA (US); Ketan P. Muni, San Jose, CA (US); Eric A. Goldfarb, Belmont, CA (US)

(73) Assignee: Acclarent, Inc., Menlo Park, CA (US)

( * ) Notice: Subject to any disclaimer, the term of this patent is extended or adjusted under 35 U.S.C. 154(b) by 0 days.

(21) Appl. No.: 13/550,293

(22) Filed: Jul. 16, 2012

(65) Prior Publication Data
US 2013/0184683 A1 Jul. 18, 2013

Related U.S. Application Data

(60) Provisional application No. 61/511,256, filed on Jul. 25, 2011.

(51) Int. Cl.
| A61M 31/00 | (2006.01) |
| A61M 3/02 | (2006.01) |
| A61B 17/24 | (2006.01) |
| A61M 25/10 | (2013.01) |
| A61M 29/00 | (2006.01) |
| A61B 17/34 | (2006.01) |
| A61B 17/16 | (2006.01) |
| A61B 19/00 | (2006.01) |
| A61B 17/00 | (2006.01) |

(52) U.S. Cl.
CPC .............. *A61M 3/0295* (2013.01); *A61B 17/24* (2013.01); *A61M 3/0283* (2013.01); *A61M 25/10* (2013.01); *A61M 29/00* (2013.01); *A61B 17/1688* (2013.01); *A61B 17/3478* (2013.01); *A61B 19/54* (2013.01); *A61B 2017/00557* (2013.01); *A61B 2217/007* (2013.01)

(58) Field of Classification Search
None
See application file for complete search history.

(56) References Cited

U.S. PATENT DOCUMENTS

| 4,195,637 A | * | 4/1980 | Gruntzig et al. ............... 604/509 |
| 4,437,856 A | * | 3/1984 | Valli .................................. 604/29 |
| 4,531,943 A | * | 7/1985 | Van Tassel et al. ............ 604/523 |
| 4,976,703 A | * | 12/1990 | Franetzki et al. .............. 604/247 |
| 5,201,723 A | * | 4/1993 | Quinn ............................ 604/264 |
| 5,409,458 A | * | 4/1995 | Khairkhahan et al. ... 604/103.08 |

(Continued)

FOREIGN PATENT DOCUMENTS

| WO | WO 2008/091652 A2 | 7/2008 |
| WO | WO 2010/033629 A1 | 3/2010 |

OTHER PUBLICATIONS

International Search Report dated Mar. 8, 2013, International Application No. PCT/US2012/046964.

*Primary Examiner* — Nicholas Evoy (57) ABSTRACT

A medical device, and a system and packaged kit containing the medical device for the treatment of a sinus opening is described. The medical device comprises a proximal end, a distal end, and a shaft system having an inflation lumen and an irrigation lumen the proximal and. The shaft system has a proximal shaft section and a distal shaft section. An inflatable balloon is attached to the distal shaft section in a position that is proximal to said distal end. The irrigation tip is distal to the balloon on the distal shaft section and has a tip opening and one or more radially facing openings. A method for treating a sinus opening includes inserting a system that includes the medical device, a sinus guide catheter and a sinus guide element into a patient's anatomy, dilating the sinus opening and irrigating a target in the nasal anatomy.

11 Claims, 6 Drawing Sheets

(56) References Cited

U.S. PATENT DOCUMENTS

| | | | |
|---|---|---|---|
| 5,498,240 A * | 3/1996 | Bagaoisan et al. | 604/96.01 |
| 5,642,730 A * | 7/1997 | Baran | 128/207.14 |
| 5,715,825 A * | 2/1998 | Crowley | 600/462 |
| 5,718,678 A * | 2/1998 | Fleming, III | 604/43 |
| 5,885,238 A * | 3/1999 | Stevens et al. | 604/6.14 |
| 5,931,730 A * | 8/1999 | Bernhardt et al. | 452/65 |
| 5,964,223 A * | 10/1999 | Baran | 128/207.14 |
| 6,117,106 A * | 9/2000 | Wasicek et al. | 604/96.01 |
| 6,126,634 A * | 10/2000 | Bagaoisan et al. | 604/101.02 |
| 6,146,416 A * | 11/2000 | Andersen et al. | 623/1.15 |
| 6,217,503 B1 | 4/2001 | Weinberger et al. | 600/3 |
| 6,293,924 B1 * | 9/2001 | Bagaoisan et al. | 604/103.07 |
| 6,319,248 B1 * | 11/2001 | Nahon | 606/22 |
| 6,500,158 B1 * | 12/2002 | Ikeguchi | 604/319 |
| 6,663,863 B2 * | 12/2003 | Horvath et al. | 424/144.1 |
| RE39,668 E * | 5/2007 | Bagaoisan et al. | 604/96.01 |
| 7,410,480 B2 * | 8/2008 | Muni et al. | 604/509 |
| 7,419,497 B2 * | 9/2008 | Muni et al. | 606/196 |
| 7,462,175 B2 * | 12/2008 | Chang et al. | 604/510 |
| 7,469,700 B2 * | 12/2008 | Baran | 128/207.14 |
| 7,472,705 B2 * | 1/2009 | Baran | 128/207.11 |
| 7,520,876 B2 * | 4/2009 | Ressemann et al. | 604/510 |
| 7,641,644 B2 * | 1/2010 | Chang et al. | 604/500 |
| 7,645,272 B2 * | 1/2010 | Chang et al. | 604/509 |
| 7,654,997 B2 | 2/2010 | Makower et al. | |
| 7,678,099 B2 * | 3/2010 | Ressemann et al. | 604/510 |
| 7,727,226 B2 * | 6/2010 | Chang et al. | 604/543 |
| 7,785,315 B1 * | 8/2010 | Muni et al. | 604/510 |
| 7,803,150 B2 | 9/2010 | Chang et al. | |
| 7,842,062 B2 * | 11/2010 | Keith et al. | 606/199 |
| 7,879,061 B2 * | 2/2011 | Keith et al. | 606/199 |
| 8,012,143 B1 * | 9/2011 | Kampa et al. | 604/532 |
| 8,029,457 B2 * | 10/2011 | Ash et al. | 604/43 |
| 8,080,000 B2 * | 12/2011 | Makower et al. | 604/510 |
| 8,088,101 B2 * | 1/2012 | Chang et al. | 604/96.01 |
| 8,114,062 B2 * | 2/2012 | Muni et al. | 604/509 |
| 8,123,722 B2 * | 2/2012 | Chang et al. | 604/104 |
| 8,267,887 B2 * | 9/2012 | Mohl | 604/102.02 |
| 8,348,969 B2 * | 1/2013 | Keith et al. | 606/199 |
| 8,381,345 B2 * | 2/2013 | Vazales et al. | 15/104.05 |
| 8,388,642 B2 * | 3/2013 | Muni et al. | 606/199 |
| 8,414,473 B2 * | 4/2013 | Jenkins et al. | 600/104 |
| 8,636,724 B2 * | 1/2014 | Wiita et al. | 604/544 |
| 8,920,402 B2 * | 12/2014 | Nash et al. | 604/523 |
| 2001/0010017 A1 * | 7/2001 | Letac et al. | 623/2.11 |
| 2001/0016705 A1 * | 8/2001 | Omaleki et al. | 604/103.06 |
| 2001/0044591 A1 * | 11/2001 | Stevens et al. | 604/6.11 |
| 2002/0010420 A1 * | 1/2002 | Bagaoisan et al. | 604/103.11 |
| 2002/0106369 A1 * | 8/2002 | Horvath et al. | 424/131.1 |
| 2002/0111584 A1 * | 8/2002 | Walker et al. | 604/113 |
| 2003/0009132 A1 * | 1/2003 | Schwartz et al. | 604/152 |
| 2003/0163148 A1 * | 8/2003 | Wang et al. | 606/159 |
| 2003/0229307 A1 * | 12/2003 | Muni et al. | 604/103.02 |
| 2004/0073162 A1 * | 4/2004 | Bleam et al. | 604/103 |
| 2004/0122456 A1 * | 6/2004 | Saadat et al. | 606/157 |
| 2004/0176837 A1 * | 9/2004 | Atladottir et al. | 623/1.35 |
| 2004/0210187 A1 * | 10/2004 | Zawacki | 604/43 |
| 2004/0267196 A1 * | 12/2004 | Miki et al. | 604/103.04 |
| 2006/0074396 A1 * | 4/2006 | Stiger | 604/509 |
| 2006/0106361 A1 * | 5/2006 | Muni et al. | 604/500 |
| 2007/0208301 A1 * | 9/2007 | Evard et al. | 604/103.1 |
| 2007/0282303 A1 * | 12/2007 | Nash et al. | 604/510 |
| 2008/0033477 A1 * | 2/2008 | Campbell et al. | 606/194 |
| 2008/0082080 A1 * | 4/2008 | Braga | 604/523 |
| 2008/0103521 A1 * | 5/2008 | Makower et al. | 606/196 |
| 2008/0183128 A1 * | 7/2008 | Morriss et al. | 604/35 |
| 2008/0234720 A1 * | 9/2008 | Chang et al. | 606/196 |
| 2008/0275483 A1 * | 11/2008 | Makower et al. | 606/192 |
| 2008/0281156 A1 * | 11/2008 | Makower et al. | 600/118 |
| 2008/0319424 A1 * | 12/2008 | Muni et al. | 604/890.1 |
| 2009/0028923 A1 * | 1/2009 | Muni et al. | 424/434 |
| 2009/0062725 A1 * | 3/2009 | Goebel | 604/22 |
| 2009/0107503 A1 * | 4/2009 | Baran | 128/204.25 |
| 2009/0187098 A1 * | 7/2009 | Makower et al. | 600/424 |
| 2009/0221988 A1 * | 9/2009 | Ressemann et al. | 604/514 |
| 2009/0260625 A1 * | 10/2009 | Wondka | 128/203.12 |
| 2009/0312745 A1 * | 12/2009 | Goldfarb et al. | 604/514 |
| 2010/0076416 A1 * | 3/2010 | Hoey et al. | 606/2 |
| 2010/0121308 A1 * | 5/2010 | Muni et al. | 604/514 |
| 2010/0145187 A1 * | 6/2010 | Weber et al. | 600/424 |
| 2010/0168511 A1 * | 7/2010 | Muni et al. | 600/104 |
| 2010/0174308 A1 * | 7/2010 | Chang et al. | 606/199 |
| 2010/0185156 A1 * | 7/2010 | Kanner et al. | 604/190 |
| 2010/0198137 A1 * | 8/2010 | Broaddus et al. | 604/28 |
| 2010/0198191 A1 * | 8/2010 | Clifford et al. | 604/514 |
| 2010/0198247 A1 * | 8/2010 | Chang et al. | 606/185 |
| 2010/0199448 A1 * | 8/2010 | Vazales et al. | 15/104.05 |
| 2010/0268245 A1 * | 10/2010 | Chang et al. | 606/108 |
| 2010/0274188 A1 * | 10/2010 | Chang et al. | 604/96.01 |
| 2010/0280450 A1 * | 11/2010 | Jain | 604/96.01 |
| 2011/0004057 A1 * | 1/2011 | Goldfarb et al. | 600/106 |
| 2011/0023887 A1 * | 2/2011 | Vazales et al. | 128/207.14 |
| 2011/0023888 A1 * | 2/2011 | Vazales et al. | 128/207.14 |
| 2011/0034828 A1 * | 2/2011 | Holmin et al. | 600/567 |
| 2011/0082483 A1 * | 4/2011 | Diamant et al. | 606/159 |
| 2011/0112512 A1 * | 5/2011 | Muni et al. | 604/514 |
| 2011/0245800 A1 * | 10/2011 | Kassab et al. | 604/506 |
| 2011/0288477 A1 * | 11/2011 | Ressemann et al. | 604/95.04 |
| 2012/0071824 A1 * | 3/2012 | Chang et al. | 604/96.01 |
| 2012/0130391 A1 * | 5/2012 | Sundt et al. | 606/108 |
| 2012/0150119 A1 * | 6/2012 | Schaeffer et al. | 604/164.06 |
| 2012/0172912 A1 * | 7/2012 | Ressemann et al. | 606/196 |
| 2012/0192872 A1 * | 8/2012 | Rudakov et al. | 128/831 |
| 2013/0019864 A1 * | 1/2013 | Wondka | 128/200.26 |

\* cited by examiner

DEVICES AND METHODS FOR TRANSNASAL DILATION AND IRRIGATION OF THE SINUSES

FIELD OF THE INVENTION

The present invention relates, in general, to medical devices and, in particular, to medical devices and related methods for the treatment of sinus conditions.

BACKGROUND OF THE INVENTION

The paranasal sinuses are hollow cavities in the skull connected by small openings, known as ostia, to the nasal canal. Each ostium between a paranasal sinus and the nasal cavity is formed by a bone covered by a layer of mucosal tissue. Normally, air passes into and out of the paranasal sinuses through the ostia. Also, mucus is continually formed by the mucosal lining of the sinuses and drains through the ostia and into the nasal canal.

Sinusitis is a general term that refers to inflammation in one or more of the paranasal sinuses. Acute sinusitis can be associated with upper respiratory infections or allergic conditions, which may cause tissue swelling and temporarily impede normal trans-ostial drainage and ventilation of the sinuses, thereby resulting in some collection of mucus and possibly infection within the sinus cavities. Chronic sinusitis is a long term condition characterized by persistent narrowing or blockage of one or more sinus ostia, resulting in chronic infection and inflammation of the sinuses. Chronic sinusitis is often associated with longstanding respiratory allergies, nasal polyps, hypertrophic nasal turbinates and/or deviated internasal septum. While acute sinusitis is typically caused by infection with a single pathogen (e.g., one type of bacteria, one type of virus, one type of fungus, etc.), chronic sinusitis is often associated with multiple pathogen infections (e.g., more than one type of bacteria or more than one genus of micro-organism).

Chronic sinusitis, if left untreated, can result in irreparable damage to the tissues and/or bony structures of the paranasal anatomy. The initial treatment of chronic sinusitis usually involves the use of drugs such as decongestants, steroid nasal sprays and antibiotics (if the infection is bacterial). In cases where drug treatment alone fails to provide permanent relief, surgical intervention may be indicated.

The most common surgical procedure for treating chronic sinusitis is functional endoscopic sinus surgery (FESS). FESS is commonly performed using an endoscope and various rigid instruments inserted through the patient's nostril. The endoscope is used to visualize the positioning and use of various rigid instruments used for removing tissue from the nasal cavity and sinus ostia in an attempt to improve sinus drainage.

A technique known as the Balloon Sinuplasty™ procedure and a system for performing the procedure has been developed by Acclarent Inc, of Menlo Park, Calif. for the treatment of sinusitis. A number of US patents and patent applications including U.S. Pat. Nos. 7,645,272, 7,654,997, and 7,803,150 describe various embodiment of the Balloon Sinuplasty™ procedure as well as various devices useable in the performance of such procedure. In the Balloon Sinuplasty™ procedure, a guide catheter is inserted into the nose and positioned within or adjacent to the ostium of the affected paranasal sinus. A guidewire is then advanced through the guide catheter and into the affected paranasal sinus. Thereafter, a dilation catheter having an expandable dilator (e.g. an inflatable balloon) is advanced over the guidewire to a position where the dilator is positioned within the ostium of the affected paranasal sinus. The dilator is then expanded, causing dilation of the ostium and remodelling of bone adjacent to the ostium, without required incision of the mucosa or removal of any bone. The catheters and guidewire are then removed and the dilated ostium allows for improved drainage from and ventilation of the affected paranasal sinus.

After performing a FESS or Balloon Sinuplasty™ procedure, it may be useful or necessary to irrigate the paranasal sinus. A device described in US 2008/0183128 may be used for irrigating a paranasal sinus. The irrigation catheter may be advanced through a guide catheter and into an ostium or the sinus for purposes of, for example irrigation, suctioning, substance delivery and culture retrieval.

There is a continuing need for improved methods and devices for treating the paranasal sinus. Although the irrigation catheter described above is easy to use, it would be useful to provide for irrigation of the sinuses during the Balloon Sinuplasty™ procedure.

SUMMARY OF THE INVENTION

Accordingly, in one aspect, the current invention is directed to a medical device for the treatment of a sinus opening, the medical device having a proximal end, a distal end, and a shaft system having an inflation lumen and an irrigation lumen between the proximal end and distal end. The shaft system has a proximal shaft section and a distal shaft section, an inflatable balloon on the distal shaft section and proximal to the distal end, and an irrigation tip on the distal shaft section, distal to the inflatable balloon. The irrigation tip has a tip opening and one or more radially facing openings.

In one embodiment, the medical device may have 3 radially facing openings. The radially facing openings may have a diameter of between 0.020 inches and 0.050 inches or of 0.026 inches.

In another embodiment, the inflation lumen and the irrigation lumen of the medical device are adjacent lumens. In further embodiments, the medical device includes a guide element lumen.

In still another embodiment, the irrigation tip has an irrigation tip lumen proximal of the atraumatic tip. The irrigation tip lumen has an irrigation tip lumen diameter, the tip opening has a tip opening diameter, and the irrigation tip lumen diameter is greater than the tip opening diameter. In another embodiment, the tip opening diameter is 0.037 inches and the irrigation lumen diameter is 0.042 inches.

In a further embodiment, the proximal shaft section of the medical device includes a stiffening member. In another embodiment, the stiffening member is a hypotube.

In another aspect, the current invention is directed to a system for accessing, dilating and irrigating a sinus, the system having a sinus guide catheter, a guiding element; and a medical device. The medical device has an inflation lumen, an irrigation lumen, an inflatable balloon and an irrigation tip. The inflation lumen and the irrigation lumen are adjacent lumens and the irrigation tip has a tip opening and at least one radially facing opening.

In one embodiment the medical device of the system has one or more direct visualization markers or one or more radiographic markers.

In another embodiment the medical device of the system has 3 radially facing openings. The radially facing openings may have a diameter of between 0.020 inches and 0.050 inches or of 0.026 inches.

In another embodiment, the system guiding element is selected from the group consisting of a guidewire or a sinus illumination system. In further embodiments, the medical device of the system includes a guide element lumen.

In other embodiments, the medical device of the system has an irrigation tip with an irrigation tip lumen proximal of the atraumatic tip. The irrigation tip lumen has an irrigation tip lumen diameter, the tip opening has a tip opening diameter, and the irrigation tip lumen diameter is greater than the tip opening diameter. In another embodiment, the tip opening diameter is 0.037 inches and the irrigation tip lumen diameter is 0.042 inches.

In a further embodiment, the medical device of the system has a proximal shaft section that includes a stiffening member. In another embodiment, the stiffening member comprises a hypotube.

In another aspect, the invention is directed to a packaged kit for treating a sinus opening. The kit comprises a medical device having an inflation lumen, an irrigation lumen, an inflatable balloon and an irrigation tip, the inflation lumen and the irrigation lumen being adjacent lumens and the irrigation tip having at least one radially facing opening, a balloon insertion stylet for insertion of the medical device into a sinus guide catheter, and irrigation tubing for connecting the medical device to a source of irrigation fluid.

In still another aspect, the invention is directed to a method for treating a target space in the nasal anatomy. The method includes providing a medical device having an inflation lumen, an irrigation lumen, an inflatable balloon and an irrigation tip. The inflation lumen and the irrigation lumen are adjacent lumens and the irrigation tip has a tip opening and at least one radially facing opening. The method includes inserting the medical device into a sinus guide catheter, inserting a guiding element into the medical device through the irrigation lumen, positioning the guide catheter in the nasal anatomy, advancing the guiding element into the target space of the nasal anatomy, advancing the medical device over the guiding element into the target space of the nasal anatomy, inflating the balloon to dilate a sinus opening, deflating the balloon, withdrawing the guiding element from the medical device, connecting irrigation tubing to the medical device, and delivering fluid to the target space though the tip opening and the at least one radially facing opening.

In one embodiment delivering the fluid occurs at a flow rate of between 50 ml/min and 200 ml/min or at a flow rate of between 75 ml/min and 125 ml/min and the sinus opening may be frontal sinus opening, a maxillary sinus opening, an ethmoid sinus opening and a sphenoid sinus opening.

In another embodiment the fluid may be water, saline, contrast agents, antimicrobial agents anti-inflammatory agents, decongestants, mucous thinning agents, anesthetic agents, analgesic agents, anti-allergenic agents, allergens, anti-proliferative agents, hemostatic agents, cytotoxic agents, and biological agents or combinations of any of the above.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, in which like numerals indicate like elements.

DETAILED DESCRIPTION

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein.

Medical devices according to embodiments of the present invention are beneficial in that, for example, their configuration provides for a particularly efficient preparation and treatment of a patient's sinus opening and is mechanically simple. Moreover, the simplicity of the medical devices provides for them to be manufactured in a cost effective manner. In addition, the medical device according to embodiments of the present invention is sufficiently stiff that it can be beneficially employed to access sinus anatomy followed by a convenient remodeling and irrigation of the sinus.

Figure 1:
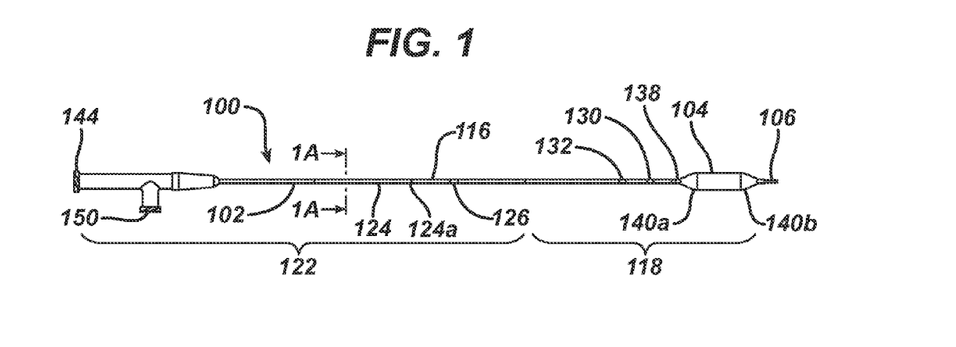
FIG. 1 is a simplified side view of a medical device according to an embodiment of the present invention.
Figure 1A:
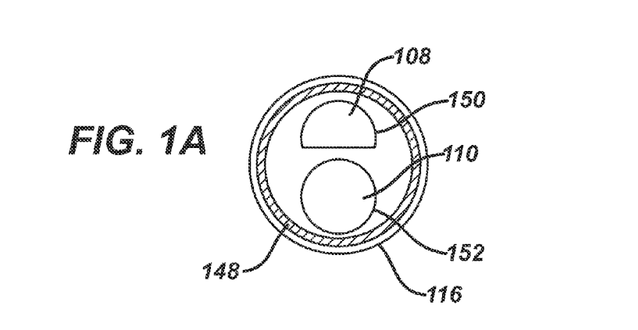
FIG. 1A is a cross section view through line 1A-1A of FIG. 1.
Figure 1B:
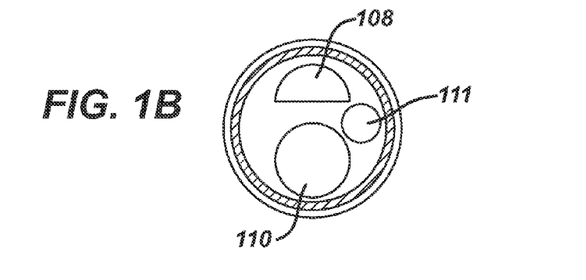
FIG. 1B is an alternative embodiment of a cross section view through line 1A-1A of FIG. 1.

FIG. 1 is a simplified side view of a medical device 100 for the treatment of a sinus opening (for example a frontal sinus opening, maxillary sinus opening, ethmoid sinus opening or sphenoid sinus opening) according to an embodiment of the present invention. Although described with regard to the sinus opening, the inventions described herein may also be useful for the dilation of the Eustachian tube, repair of endo-cranial fractures, airway procedures such as subglottic stenosis dilation and other procedures of the ear, nose and throat. The medical device 100 is a sinus remodeling and irrigation catheter with an integrated shaft system 102 and a high pressure balloon 104 near the irrigation tip 106. The shaft system 102 contains adjacent dual lumen tubing (see FIG. 1A). By adjacent dual lumen tubing is intended that the lumens are next to each other but are spaced apart, one from the other. The inflation lumen 108 is used for inflation of the balloon with water, contrast medium or saline through inflation port 150, and the irrigation lumen 110 permits passage of a guidewire or sinus illumination system to facilitate advancement of the medical device 100 to the target site and, further, to allow for the flow of irrigation fluid (water or saline) to the target site. In an alternative embodiment, there may be provided a third lumen, a guide element lumen 111, such lumen being adjacent to the inflation lumen 108 and the irrigation lumen 110 (see FIG. 1B). The irrigation lumen 110 and the guide element lumen 111 merge into a single irrigation lumen 110 in the distal shaft portion 118 of the device, proximal to the balloon 104. The medical device 100 has an irrigation tip 106 with both a forward facing tip opening 114 and radially facing openings 112a, 112b and 112c to facilitate irrigation delivery through the irrigation lumen 110. The medical device 100 is intended to dilate sinus ostia and spaces within the paranasal sinus cavities and to provide a means to irrigate from within a target sinus for diagnostic and therapeutic purposes. The medical device 100 is designed to irrigate the sinus through the tip opening 114 and three radially facing openings 112a, 112b and 112c in the irrigation tip 106, by delivering fluid via the irrigation lumen 110 for delivery before, during, or after dilation of the sinus ostia or spaces within the paranasal sinus cavities. Further, instead of delivering fluid through the irrigation lumen 110, a vacuum may be applied and a culture may be obtained by suctioning through the tip opening 114 or the radially facing openings 112a, 112b and 112c. By radially facing openings is intended that the flow through the openings may be at 90 degrees from the flow through the tip opening, but is may also be at 30, 45 or 60 degrees or other angles between 0 and 90 degrees, and the openings may be round or non-round such as oval or slot-shaped.

The sinus balloon 104 is designed to be non-compliant or semi-compliant. The diameter of the non-compliant balloon does not vary significantly with inflation pressure and that of the semi-compliant balloon will vary only to the extent that it will "hourglass" or "dog-bone" about a target region. The balloon itself may be any shape such as round, triangular, oval or square. In the embodiment shown in FIG. 1, the balloon is round and semi-compliant. A stiffening member (in this case a hypotube 116) is incorporated on the proximal end of the medical device (at the distal end of the proximal shaft portion 122) to provide rigidity during insertion through a sinus guide catheter, as further described below.

As shown in FIG. 1 in some embodiments, direct visualization markers and/or radiographic markers may be disposed along the integrated shaft system 102. Generally, "direct visualization markers" refers to markers that may be viewed during use with the naked eye or by use of an endoscope, while radiographic markers include radiopaque material and are viewed using a radiographic device such as intra-operative fluoroscopy. In one embodiment, at the distal end, there is a first distal radiographic marker 120a, which has a proximal edge aligned with the location where the proximal taper 140a of the balloon 104 meets the proximal end of the effective length 142 of the balloon 104. There is also a second distal radiographic marker 120b, which has a distal edge aligned with the location where the distal taper 140b meets the distal end effective length 142 of the balloon 104. The distance across the outside edges of the distal markers 120a and 120b represents the effective length 142 of the balloon 104. The distal markers 120a and 120b may be platinum marker bands. In this embodiment, the distal markers help to ensure that the medical device 100 is in a straight position inside the guide during the device loading and preparation. Additional radiographic markers may be included along the shaft of the catheter and/or at the distal tip.

Direct visualization markers can be positioned in a number of locations along the integrated shaft system 102. Although one embodiment is described here with reference to FIGS. 1 and 2, other variations may be substituted in alternative embodiments. In one embodiment, shaft system 102 may have a dark color, such as black, dark blue, dark grey or the like, and markers may have a light color, such as white, green, red or the like. In some embodiments, markers may have different colors and/or different widths to facilitate distinguishing the markers from one another during use. This contrast in colors may facilitate viewing the markers in a darkened operation room and/or when using an endoscope inside a patient in the presence of blood.

Figure 2:
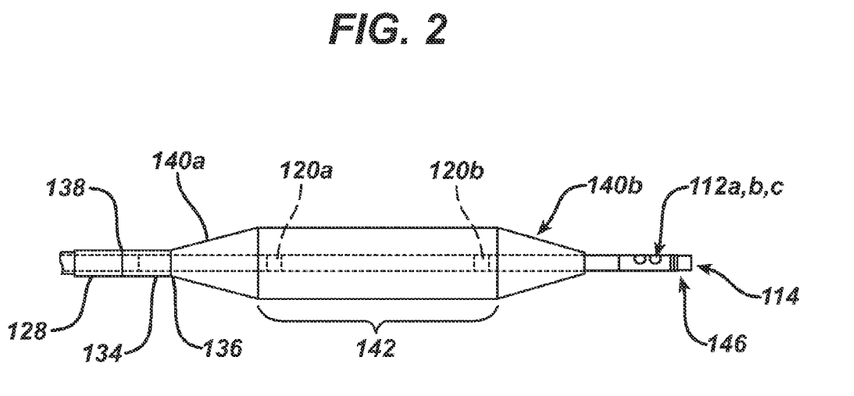
FIG. 2 is an enlarged view of the distal end of the medical device shown in FIG. 1.

In one embodiment, there may be a first distal shaft marker 128 (or "endoscopic marker," since it is typically viewed during use via an endoscope) disposed on the distal shaft portion 118 of the shaft system 102 at a location such that its distal edge aligns with the location where the proximal taper 140a of the balloon 104 meets the shaft system 102. The extended balloon neck 134 allows the first endoscopic marker 128 to be placed on the shaft and away from any adhesive bonding used to secure the proximal end of the balloon neck to the shaft. The first endoscopic marker 128 indicates to the user the ending location of the balloon 104 and indicates that the balloon has exited the guide during a procedure. In one embodiment, the first endoscopic marker 128 may be about 2 mm wide.

A second distal shaft marker 130 is disposed on the shaft system 102 such that the distal edge of the marker is 1 cm.±.0.2 cm from the location where the proximal taper 140a of the balloon 104 meets the shaft system 102. This marker indicates to the user that the shaft location is 1 cm away from the end of the balloon indicating that the balloon has extended from the guide during the procedure. In one embodiment, the second distal shaft marker may be about 2 mm wide and white in color, while the first marker is about 2 mm and green in color. Of course, any of a number of different size and color combinations may be used alternatively.

A third distal shaft marker 132 is disposed on the shaft system 102 such that the distal edge of the marker is 1 cm.±.0.1 cm from the distal edge of the second distal shaft marker 130. As shown in FIG. 1, the third distal shaft marker is a double marker to distinguish the second and third distal shaft markers 130 and 132 one from one another. The third distal shaft marker 132 indicates the shaft location 2 cm away from the end proximal end of the balloon 104, thus indicating the distance the balloon has extended from the guide during the procedure. In one embodiment, the two markers forming the third distal shaft marker 132 are each 0.75 mm wide and white in color, however, the size and color of the marker can be changed in alternative embodiments. The differences in the first, second and third distal shaft markers' color, length and number of marks give the indication of the relative location proximal to the balloon under endoscopic visibility. Using an endoscope, the physician user can identify the length of catheter that has been advanced and retracted out of a guide catheter and/or can approximate a location of the balloon 104 relative to patient anatomy such as a paranasal sinus ostium, other paranasal sinus opening, or other openings in the ear, nose or throat. This approximation of balloon position may be very useful in circumstances when the balloon 104 has been advanced far enough into an anatomical location that the balloon 104 can no longer be viewed via endoscope. For example, using the three endoscopic markers, the user is able to endoscopically gauge the distance the catheter has advanced into the frontal recess once the proximal portion of the balloon is no longer visible. Of course, in alternative embodiments, distal shaft markers having different numbers, sizes, colors and positions along the catheter shaft may be used.

In some embodiments, in addition to one or more distal shaft markers, one or more proximal shaft markers may be disposed along the proximal portion 122 of shaft system 102. In general, such proximal shaft markers may be viewed directly by a physician, without using an endoscope, to indicate to the physician a location of the balloon 104 of the medical device 100 relative to a guide catheter (see i.e. catheter 200a in FIG. 3) through which the medical device 100 is being advanced. As with the distal shaft markers, the proximal shaft markers may have any suitable width, color, number, position and the like. In one embodiment, for example, as shown in FIG. 1, two proximal shaft markers 124, 126 may have a light color to contrast with a dark colored shaft system 102 and increase visibility in a darkened operating room. The more proximal of the proximal markers 124 (or the "first proximal shaft marker") may indicate that a tip of the medical device 100 is at a distal end of the guide catheter 200 and that the balloon 104 has exited the distal end 202 of the guide catheter as the marker 124 passes into the proximal end 204 of the guide catheter. The more distal of the proximal markers 126 (or the "second proximal shaft marker") may indicate to a user that the balloon 104 is just proximal to a curve 206 in a guide catheter when marker 126 is located at the proximal end 204 of the guide catheter.

In one embodiment, the first proximal shaft marker 124 is disposed on the shaft system 102 such that the length from the proximal end of the proximal balloon taper 140a to the proximal end of the first shaft marker 124 is 13.1 cm.±.0.2 cm. The length of the first proximal shaft marker 124 can vary depending on the size of the balloon catheter and may be determined by adding the length of the irrigation tip 106, the effective or working length 142 of the balloon 104, and the lengths of the two balloon taper sections 140a and 140b. Also, the first proximal shaft marker 124 is preferably white in color, however, other light colors, such as grey, can be used as well.

The second proximal shaft marker 126 is disposed on the shaft system 102 distally from the first proximal shaft marker 124. The second proximal shaft marker 126 is positioned such that the irrigation tip 106 of the medical device 100 is 11.4 cm.±.0.2 cm from the distal edge of the second proximal shaft marker 126. Also, the second proximal shaft marker 126 has a length of 3 mm.±2 mm. It is preferred that the second shaft proximal marker 126 is white in color, however, other light colors, such as grey, can be used as well.

Figure 3:
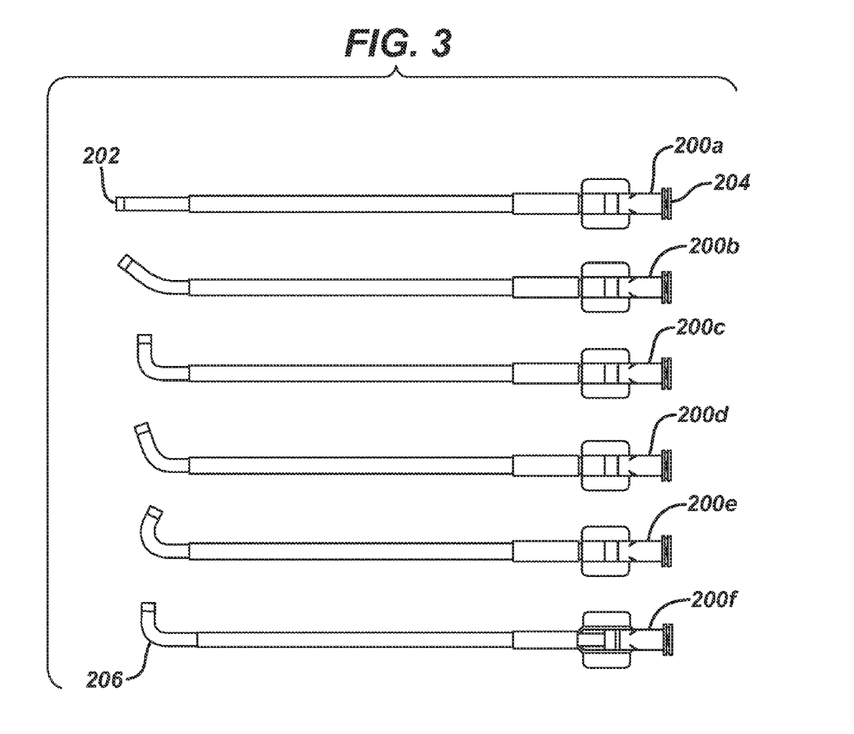
FIG. 3 shows a collection of sinus guide catheters useful for positioning of the sinus balloon catheters of the invention.

When the medical device 100 is inserted into a guide catheter 200a, a user may visualize the first and second proximal shaft markers 124 and 126 to determine the position of the irrigation tip 106 and the balloon 104 of the medical device 100 relative to the sinus guide catheter 200a. For instance, when the second proximal shaft marker 126 is aligned with the proximal opening 204 of the guide catheter, the user will know that the balloon 104 is proximal to the curve 206 of the guide catheter. The position of the second proximal shaft marker 126 helps to visually ensure that the medical device 100 is properly loaded into the sinus guide catheter 200a. When the distal edge of the first proximal shaft marker 124 is aligned with the proximal opening 204 of the guide catheter 200a, the user knows that the irrigation tip 106 of the medical device 100 is beginning to exit the guide catheter 200a, and when the proximal edge of the first proximal shaft marker is aligned with the proximal opening 204 of the guide catheter 200a, the user knows that the balloon is completely out of the guide catheter 200a.

The visible markers 124, 126, 128, 130 and 132 are preferably light in color, such as white as indicated above, to contrast with a dark color of the shaft system 102, which is preferably black. The high contrast between these visible markers and the shaft helps view the markers in a low light environment. Also, the high contrast allows the user to view directly with an endoscope the markers and know where the balloon 104 is located relative to a sinus ostium. Furthermore, the color contrast is useful during the procedure when the field is full of blood and/or mucus to view the markers and know the position of the balloon. Of course, any other suitable contrasting color combination may be used. In one embodiment, for example, the shaft system 102 may be light colored, and the markers 124, 126, 128, 130 and 132 may be dark colored.

FIG. 3 shows a series of sinus guide catheters 200a-200f that may be used in conjunction with the medical device 100. These guide catheters 200a-200f are substantially rigid and each has a preset distal curve of 0 degrees (200a), 30 degrees (200b), 90 degrees (200d), 70 degrees (200c) or 110 degrees (200e and 200f). Different curvatures are useable to access the ostia of different sinuses. For example, a 70 degree guide is typically used to access the ostium of a frontal sinus, a 90 or 110 degree guide is typically used to access the ostium of a maxillary sinus, etc. Each of these guide catheters 200a-200f has a length of 12.7 cm. These sinus guide catheters are described in U.S. patent application Ser. Nos. 10/944,270 and 11/355,512 and U.S. Pat. Nos. 7,654,997 and 7,803,150 which are hereby incorporated by reference, and are commercially available as Relieva™ sinus guide catheters from Acclarent, Inc., Menlo Park, Calif.

Figure 4:
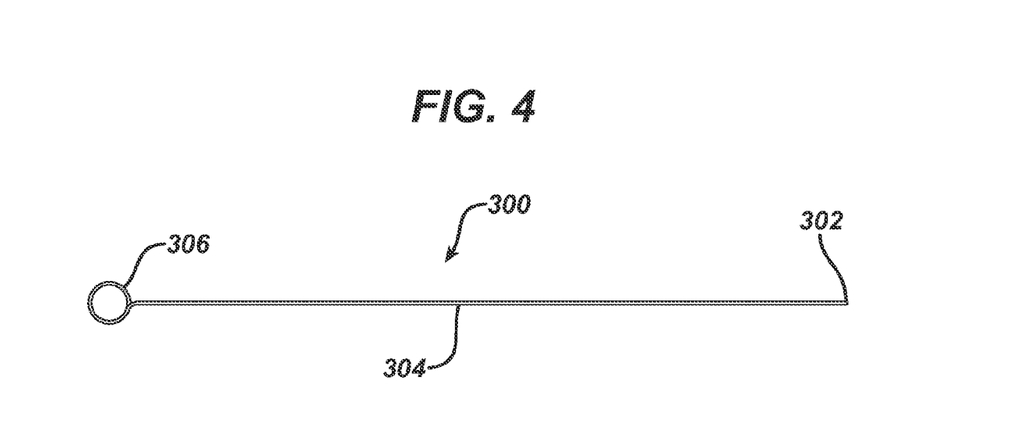
FIG. 4 shows a stylet for positioning the medical devices of the invention.
Figure 5:
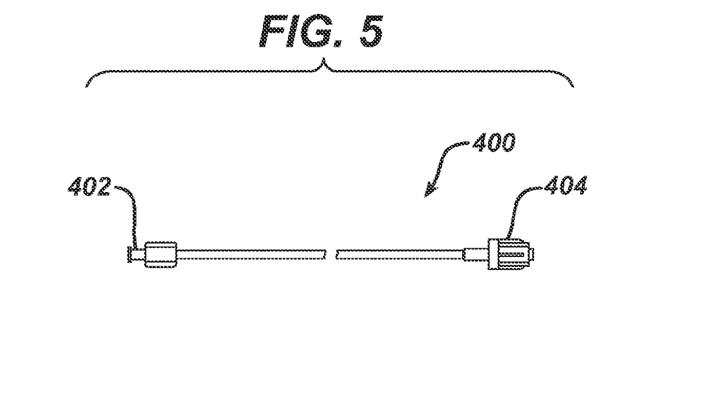
FIG. 5 shows irrigation tubing useful with the medical devices according to the invention.
Figure 8:
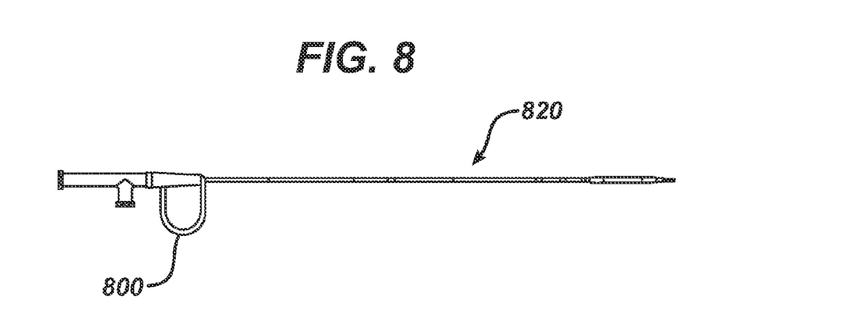
FIG. 8 is a side view of a medical device according to an embodiment of the present invention.

The medical device 100 is packaged with a balloon insertion stylet 300 (see FIG. 4) and irrigation tubing 400 (see FIG. 5). The stylet 300 comprises a rounded distal tip 302, a support shaft 304 and a proximal loop 306. The insertion stylet 300 assists with insertion of the medical device 100 into the sinus guide catheter 200a and is removed from the device 100 prior to advancement of the medical device 100 into the patient anatomy. The irrigation tubing 400 incorporates standard luer connectors 402 and 404 on each end and is used to attach a sterile syringe to the irrigation port 144 of the medical device 100 for sinus irrigation. Additionally, as shown in FIG. 8, a ring 800 is provided that may be operated by the thumb or finger of a user to aid in insertion of the medical device 820.

Figure 6:
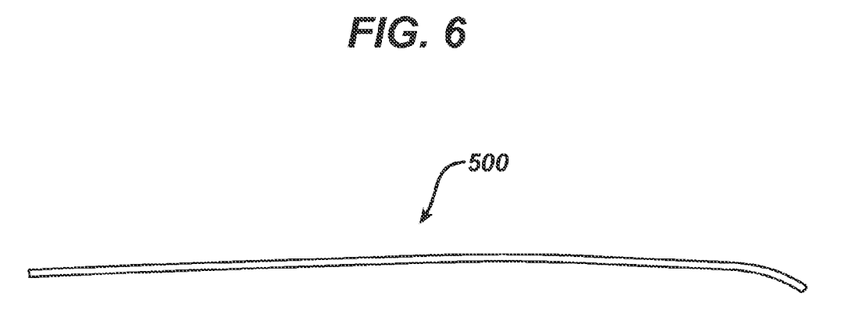
FIG. 6 is a perspective view of a guidewire for use with the medical devices of the invention.
Figure 7:
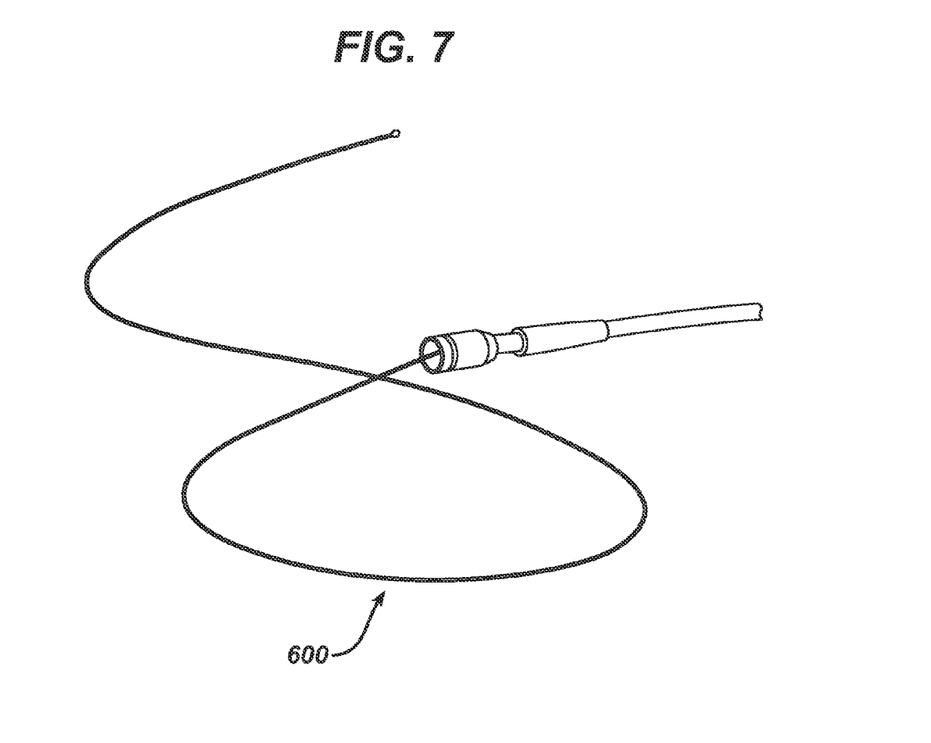
FIG. 7 is a perspective view of a sinus illumination system for use with the medical devices of the invention.

In the following description, the sinus guide catheter will be referred to as 200a, but any of the guide catheters 200b-f shown in FIG. 3 may be used. Following insertion of the medical device 100 into the sinus guide catheter 200a, a guiding element such as a sinus guidewire 500 (i.e. Relieva Vigor® Sinus Guidewire manufactured by Acclarent Inc, Menlo Park, Calif. and shown in FIG. 6) or sinus illumination system 600 (i.e. Relieva Luma Sentry™ Sinus Illumination System shown manufactured by Acclarent Inc, Menlo Park, Calif. and shown in FIG. 7) is inserted through the irrigation port 144 of the medical device 100 and to the distal tip of the sinus guide catheter 200a. Sinus access is achieved by positioning the sinus guide catheter 200a in the nasal anatomy, and advancing the sinus guidewire 500 or sinus illumination system 600 into the target sinus. Once sinus access has been achieved, the medical device 100 is advanced over the sinus guidewire 500 or sinus illumination system 600 and into the target space. The endoscopic markers on the balloon catheter can be used to assist with placement. The medical device 100 is then inflated to dilate the sinus ostia. Following dilation, the balloon is deflated. The guidewire 500 or sinus illumination system 600 is removed from the nasal anatomy. A standard syringe is connected to the irrigation tubing 400, which is connected to the irrigation port 144 of the medical device 100. Fluid is manually delivered to the sinus through the irrigation tip 106 via the distal tip opening 114 and three radially facing openings 112a, 112b and 112c of the medical device 100, each side port having a diameter of 0.026 inches. Upon completion, the medical device 100 is retracted into the sinus guide catheter 200*a* and removed from the anatomy. The medical device 100 can be prepared for additional sinus dilations and/or irrigations in the same patient. Alternatively, a suction system such as a standard syringe or other vacuum source such as a vacuum pump may be connected to the irrigation port 144 either directly and through a tubing system and the target sinus may be suctioned either before or after treatment thereof.

The medical device 100 sizes may be 3.5 mm×12 mm, 6 mm×16 mm or 7 mm×24 mm, although others are within the scope of the invention, including, but not limited to 5 mm×16 mm, 5 mm×24 mm or 7 mm×16 mm. The distal shaft portion or section 118 of the device has an inner diameter of ≥0.037 inches and the proximal shaft portion or section 122 of the device has an inner diameter of 0.042 inches. The distal edge 138 of the first endoscopic marker 128 is located 10 mm from the proximal edge 136 of the proximal balloon taper 140*a*, the length from the medical device tip opening 114 to the distal end 124*a* of the first shaft marker 124 is 114 mm and the distance from the proximal end 136 of the proximal balloon taper 140*a* to the proximal end 124*a* of the shaft marker 124 is 131 mm. The total length of the 3.5 mm medical device is 250 mm and of the other medical devices is 252 mm. The balloon inflated diameters for the medical devices are as follows: 3.5 mm for the 3.5 mm×12 mm, 6 mm for the 6 mm×16 mm and 7 mm for the 7 mm×24 mm. The balloon inflated working lengths for the medical devices are as follows: 12 mm for the 3.5 mm×12 mm, 16 mm for the 6 mm×16 mm and 24 mm for the 7 mm×24 mm. The maximum outer shaft diameter is ≤0.086 inches. The deflation time of the balloon catheter is preferably seconds. The irrigation flow rate is approximately 100 ml/min and may between ≤50 and 200 ml/min or 75 and 125 ml/min with a maximum flow rate of 250 ml/min.

The balloon 104 is made of any suitable material known in the art for inflation balloons and may be constructed of compliant, semi-compliant or non-compliant materials such as nylon (semi-compliant) and polyethylene terepththalate (PET) (non-compliant). In a particular embodiment, the balloon is constructed of semi-compliant material such as nylon. The atraumatic tip portion 146 is also made of nylon and is soft with a durometer of less than approximately 55 D (often approximately 40 D). The remainder of the irrigation tip is less soft (with a durometer greater than about 55 D, often about 70 D) than the tip portion 146 and is flexible with a longer length than prior art balloons tips in order to accommodate the radially facing openings 112*a*, 112*b* and 112*c*. In this way, the medical device 100 is more easily inserted into the guide catheter 200*a* and through the tortuous sinus anatomy. The atraumatic tip portion 146 may further contain a marker that is nylon with 20% barium sulfate and is approximately 1 mm in length or may contain any other type of radiopaque marker for fluoroscopic visualization or colored marker for direct visualization of the patient anatomy. In the particular embodiment shown in FIG. 1A, the outer shaft 148 of the medical device 100 is made of pebax. The first inner shaft 150 (comprising the inflation lumen) and the second inner shaft 152 (comprising the irrigation lumen) are made of nylon and pebax. The hypotube shaft 116 that surrounds the outershaft 148 is 304 stainless steel. The combination of materials (the nylon balloon and the adjacent dual lumen design) provides for ease of insertion of the medical device into and removal from the guide catheter 200*a* (at least in part due to the smaller profile of the nylon balloon) and navigation through the tortuous sinus anatomy. Insertion into the guide catheter 200*a* and navigation through the tortuous anatomy is also enhanced by the atraumatic tip that is long, soft and flexible.

Medical device 100 is configured to irrigate or suction fluids deep within the sinuses, as well as other areas within the paranasal space. Medical device 100 is sized appropriately to be delivered into adult as well as pediatric sinuses, including maxillary, sphenoid, ethmoid and frontal sinuses. Further, the devices of the invention may be useful for the treatment of the Eustachian tube or through an incision to access the middle ear. Medical device 100 can also be used to deliver diagnostic or therapeutic substances into the sinuses or other areas in the paranasal space. Examples of such diagnostic or therapeutic substances include, but are not limited to: contrast agents, pharmaceutically acceptable salt or dosage form of an antimicrobial agent (e.g., antibiotic, antiviral, anti-parasitic, antifungal, etc.), a corticosteroid or other anti-inflammatory (e.g., an NSAID), a decongestant (e.g., vasoconstrictor), a mucous thinning agent (e.g., an expectorant or mucolytic), an anesthetic agent with or without vasoconstrictor (e.g., Xylocaine with or without epinephrine, Tetracaine with or without epinephrine), an analgesic agent, an agent (anti-allergenic agent) that prevents of modifies an allergic response (e.g., an antihistamine, cytokine inhibitor, leucotriene inhibitor, IgE inhibitor, immunomodulator), an allergen or another substance that causes secretion of mucous by tissues, anti-proliferative agents, hemostatic agents to stop bleeding, cytotoxic agents e.g. alcohol, and biological agents such as protein molecules, stem cells, genes or gene therapy preparations.

Referring now to FIG. 1, in one embodiment, medical device may include a forward facing tip opening 114 three radially facing openings 112*a*, 112*b*, and 112*c*, on irrigation tip 106 spaced 120 degrees apart, with the inner diameter of the forward facing tip opening being 0.037 inches and each of the side openings having a inner diameter of 0.026 inches and the inner diameter of the irrigation lumen proximal of the atraumatic tip is about 0.042 inches. Alternative embodiments may include any suitable alternative number of side openings distributed in any suitable pattern such as a helical pattern. In one embodiment, a first side opening may be placed at about 2.5 mm from the distal end of medical device 100, a second side opening may be placed at about 3.5 mm from the distal end of medical device 100, and a third side opening may be placed at about 4.5 mm from the distal end of medical device 100, with each of these measurements being from the distal end to approximately the center of each side opening. The length of the irrigation tip from the distal end of the medical device 100 to the distal end of the balloon 104 is approximately 7 mm. Each side opening may have any suitable diameter in various alternative embodiments. For example, in one embodiment, each side opening may have a diameter of between about 0.020 inches and about 0.050 inches and or between about 0.030 inches and about 0.040 inches and or about 0.033 inches, so long as the diameter of the irrigation lumen of the irrigation tip proximal of the atraumatic tip is larger than the diameter of the forward facing tip opening.

In an alternative embodiment, the medical device 100 may contain an integrated guidewire such that there is no irrigation from the distal end of the device, but only from the radially facing openings.

The invention has been described with reference to certain examples or embodiments of the invention, but various additions, deletions, alterations and modifications may be made to those examples and embodiments without departing from the intended spirit and scope of the invention. For example, any element or attribute of one embodiment or example may be incorporated into or used with another embodiment or example, unless otherwise specified or if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

What is claimed is:

1. A medical device for the treatment of a sinus opening, the medical device comprising:
    a proximal end:
    a distal end;
    a shaft system having an inflation lumen, a guide element lumen and an irrigation lumen between said proximal end and said distal end, said shaft system having a proximal shaft section and a distal shaft section;
    an inflatable balloon having an inflation diameter of between 3.5 mm and 7 mm and an inflation length of between 12 mm and 24 mm on said distal shaft section and proximal to said distal end; and
    an irrigation tip on said distal shaft section, distal to the inflatable balloon, said irrigation tip comprising a tip opening and one or more radially facing openings
    wherein the guide element lumen merges into the irrigation lumen in the distal shaft section of the shaft system.

2. The medical device of claim 1 wherein the one or more radially facing openings comprise 3 openings.

3. The medical device of claim 2 wherein the radially facing openings have a diameter of between 0.020 inches and 0.050 inches.

4. The medical device of claim 3 wherein the radially facing openings have a diameter of 0.026 inches.

5. The medical device of claim 2 wherein the radially facing opening are spaced 120 degrees apart.

6. The medical device of claim 1 wherein the inflation lumen and the irrigation lumen are adjacent lumens.

7. The medical device of claim 1 wherein the irrigation tip comprises an atraumatic tip portion.

8. The medical device of claim 7 wherein the irrigation tip has an irrigation tip lumen proximal of the atraumatic tip, said irrigation tip lumen having an irrigation tip lumen diameter; and
    wherein the tip opening has a tip opening diameter; and
    wherein the irrigation tip lumen diameter is greater than the tip opening diameter.

9. The medical device of claim 8 wherein the tip opening diameter is 0.037 inches and the irrigation lumen diameter is 0.042 inches.

10. The medical device of claim 1 wherein the proximal shaft section further comprises a stiffening member.

11. The medical device of claim 10 wherein the stiffening member comprises a hypotube.

* * * * *